US00PP11253P

United States Patent [19]

Hofmann

[11] Patent Number: Plant 11,253

[45] Date of Patent: Feb. 29, 2000

[54] GERANIUM PLANT NAMED 'AURALIA'

[75] Inventor: Christa Hofmann, Grossdittmannsdorf, Germany

[73] Assignee: Elsner Pac Jungpflanzen, Germany

[21] Appl. No.: 08/909,615

[22] Filed: Aug. 12, 1997

[51] Int. Cl.[7] ..... A01H 5/00

[52] U.S. Cl. ..... Plt./329

[58] Field of Search ..... Plt./87.12, 324, Plt./325, 328, 329

[56] References Cited

U.S. PATENT DOCUMENTS

P.P. 9,216 7/1995 Klemm ..... Plt./87.12

P.P. 9,217 7/1995 Trees ..... Plt./87.12

OTHER PUBLICATIONS

UPOV–ROM, 1998/01, Plant Variety Database, GTI Jouve Retrieval Software, 6 citations for 'Auralia'.

*Primary Examiner*—Howard J. Locker
*Attorney, Agent, or Firm*—Webb Ziesenheim Logsdon Orkin & Hanson, P.C.

[57] ABSTRACT

This variety has a unique bright pink flower which contrasts with the dark green foliage. The variety provides an abundance of cuttings and roots with ease. The flowers are large and recovery time after poor weather is minimal. The plant grows well in containers or as ground plantings.

1 Drawing Sheet

BACKGROUND OF THE NEW PLANT

The present invention comprises a new and distinct cultivar of *Pelargonium×hortorum* named 'Auralia'. The plant is being marketed in the United States as 'Sweet Temptation'. The new variety was discovered in a selected breeding program in Dresden, Germany in 1986. The new variety is a selection from the crossbreeding of several breeding lines which are unnamed but which include cross number 6K-8-1. The breeding lines are maintained proprietary for breeding purposes. The new variety was first asexually reproduced by cuttings at Dresden, Germany shortly after discovery. The new variety has been asexually reproduced by cuttings at Oglevee Ltd. in Connellsville, Pa. since Jan. 12, 1993. It has also been trial and field tested at Connellsville, Pa. and has been found to retain its distinctive characteristics through successive propagations.

The cultivar, when grown in a glass greenhouse in Connellsville, Pa. using natural light and 60° F. night temperature and 68° F. day temperature, has a response time of six weeks from a rooted cutting to finishing in a 10 cm pot. The response time was determined on plants grown in soilless media employing constant fertilizer at 200–250 parts per million nitrogen and potassium in full light.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected by asexual reproductions carried out by Oglevee Ltd. in Connellsville, Pa. The plant history were taken on six week plants blossomed under natural light in a greenhouse and the color ratings were taken indoors under 200–250 foot candles of florescent cool white light. The color references are primarily to the R.H.S. Colour Chart of The Royal Horticultural Society of London.

THE PLANT

Classification:
- *Botanical.*—*Pelargonium×hortorum.*
- *Commercial.*—Florists' Zonal Geranium Form: Medium, mound habit; uniform.
Height: 23 to 26 cm. from top of pot.
Growth: Free basal branching.
Strength: Free and early flowering, needs no artificial support.
Foliage: Stalked leaf attachment; very dark green foliage.
Leaves:
- *Size.*—6.5 to 7 cm. across.
- *Shape.*—Reniform; cordate base.
- *Margin.*—Crenate.
- *Texture.*—Leathery, pubescent, shiny.
- *Color.*—Top: Green Group 137A. Bottom: Green Group 137C. Zone: Green Group 137B.

Ribs and veins:
- *Venation.*—Palmate.
- *Color.*—Green Group 143C.

Petioles:
- *Length.*—6 to 8.5 cm.
- *Color.*—Green Group 143C.

Stem:
- *Color.*—Green Group 143C.
- *Internode length.*—2 to 3 cm. in length.

THE BUD (UMBEL)

Shape: Elliptical cluster.
Size: 3 to 3.5 cm. across.

INFLORESCENCE

Blooming habit: Semidouble; continuous; free and early flowering.
Borne umbel: Florets on pedicel; pedicel on peduncle; 7 to 9 cm. above foliage.
Closed florets: Bud size: 1 to 1.5 cm.
Size: Fully Open Bloom: 4 to 5.5 cm. across.
Open florets:
- *Form.*—Ruffled; slightly cupped.

*Color.*—Top: Yellow-White Group 158D at the eye at base moving to Red-Purple Group 68B at the middle and Red Purple Group 68A at the edge. Bottom: Red Purple Group 68B at outer edge to Red Purple 68C at middle-white at base. Veining of darker pink showing through.

Petals: 8 to 10 in number.

Petal size:

*Length.*—2.2 to 2.5 cm.

*Width.*—1.7 to 1.8 cm.

Number of florets per umbel: 9 to 22.

Texture and appearance: Smooth, satiny, reflective, tonality from a distance bright, clear, candy pink flowers with white centers set above a dark green mound of foliage.

Petaloids:

*Quantity.*—3 to 4.

*Shape.*—Twisted, irregular.

*Color.*—Top: Red Purple Group 68A. Bottom: Red Purple Group 68D.

Pedicel:

*Length.*—3 to 3.5 cm.

*Color.*—Greyed Purple Group 183B.

Peduncle:

*Length.*—20 to 23 cm.

*Color.*—Green Group 143C and Greyed Purple Group 183B.

Disease resistance: Not known.

Lastingness of the bloom: 7 to 14 days.

Fragrance: None detected.

REPRODUCTIVE ORGANS

Stamens:

*Anthers.*—2 mm. in length.

*Filaments.*—7 to 8 mm. in length.

*Color.*—Pink-Red Purple Group 57B.

*Pollen.*—Golden Brown.

Pistils:

*Number.*—1.

*Length.*—7 to 8 mm.

*Stigma.*—Color: Pink-Red Purple Group 57B.

*Style.*—2 to 3 mm. in length.

*Ovaries.*—Color: Green; superior pubescent.

*Length.*—4 mm.

Fruit: None observed.

GENERAL CHARACTERISTICS

The bright pink flower contrasts with the very dark green foliage. The new variety does well in the greenhouse providing an abundance of cuttings; roots with ease and finished nicely in a 10 cm. pot. The variety also grows in a container as well as in ground plantings. The large amount of flowers and the quick recovery time after poor weather are additional features of the plant.

I claim:

1. A new and distinct variety of Geranium plant substantially as shown and described.

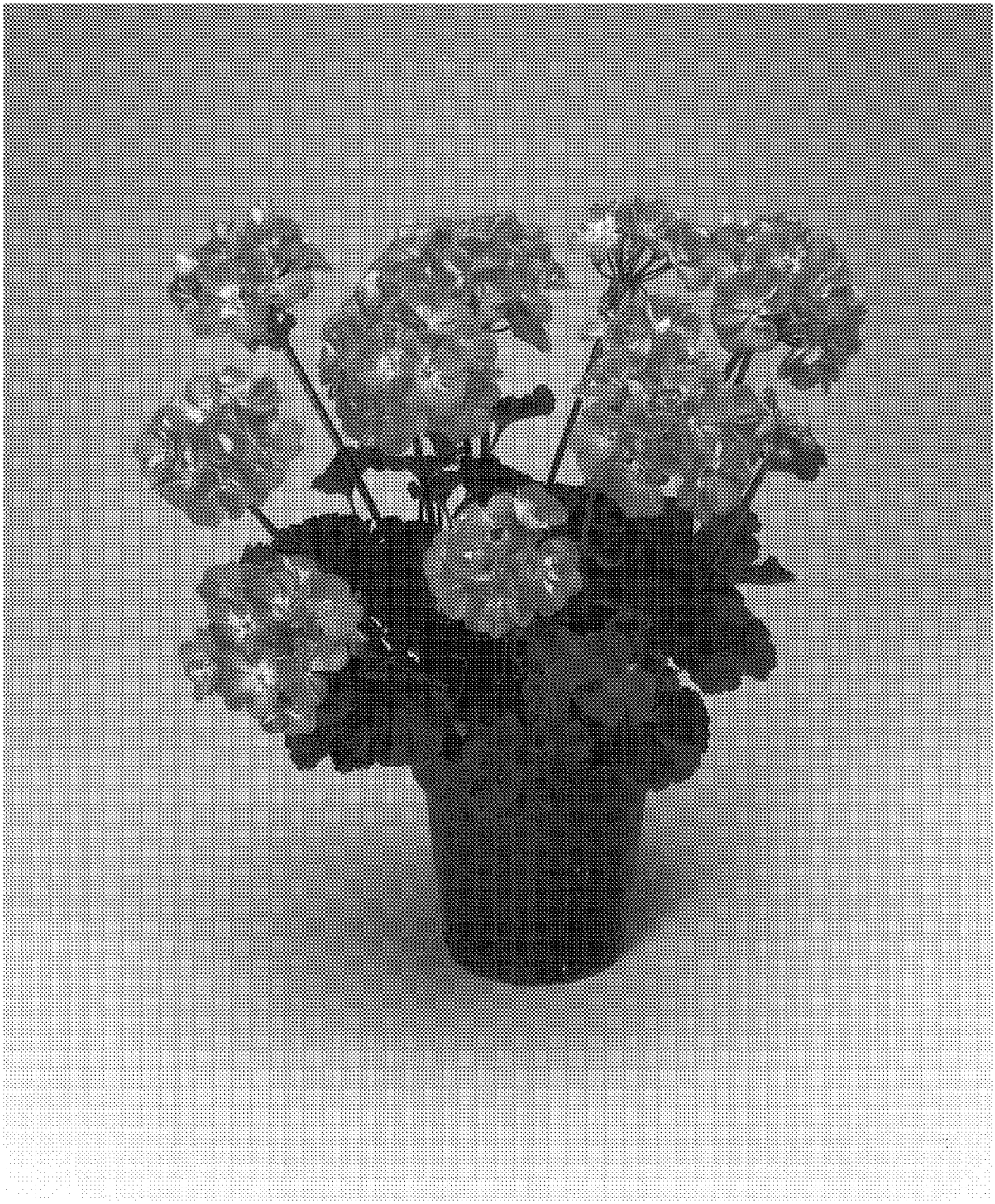

* * * * *